United States Patent
Uluyol

(10) Patent No.: US 7,531,137 B2
(45) Date of Patent: May 12, 2009

(54) SUBSTANCE DETECTION SYSTEM

(75) Inventor: Onder Uluyol, Fridley, MN (US)

(73) Assignee: Honeywell International Inc., Morristown, NJ (US)

( * ) Notice: Subject to any disclaimer, the term of this patent is extended or adjusted under 35 U.S.C. 154(b) by 1013 days.

(21) Appl. No.: 10/836,769

(22) Filed: Apr. 30, 2004

(65) Prior Publication Data
US 2005/0244978 A1 Nov. 3, 2005

(51) Int. Cl.
*G01N 7/00* (2006.01)
(52) U.S. Cl. .............. 422/83; 422/98; 702/22; 702/23; 702/24; 702/25; 702/32
(58) Field of Classification Search ............ 422/68.1, 422/82.01, 82.02, 83, 93, 98; 436/149, 150; 702/19–24, 30, 32
See application file for complete search history.

(56) References Cited

U.S. PATENT DOCUMENTS

| | | | |
|---|---|---|---|
| 4,399,687 A | | 8/1983 | Collins |
| 5,675,070 A | | 10/1997 | Gelperin |
| 5,918,257 A | | 6/1999 | Mifsud et al. |
| 6,212,938 B1 | | 4/2001 | Staples |
| 6,418,783 B2 * | | 7/2002 | Sunshine et al. ........... 73/29.01 |
| 6,422,061 B1 * | | 7/2002 | Sunshine et al. ........... 73/29.01 |
| 6,450,008 B1 | | 9/2002 | Sunshine et al. |
| 6,467,333 B2 | | 10/2002 | Lewis et al. |
| 6,481,773 B1 * | | 11/2002 | Salani et al. .............. 296/37.16 |
| 6,495,102 B1 | | 12/2002 | Suslick et al. |
| 6,627,154 B1 * | | 9/2003 | Goodman et al. ........ 422/82.01 |
| 6,967,612 B1 * | | 11/2005 | Gorman et al. ................ 342/22 |
| 7,034,677 B2 * | | 4/2006 | Steinthal et al. ........ 340/539.12 |
| 2001/0039824 A1 | | 11/2001 | Sunshine et al. |
| 2001/0048072 A1 | | 12/2001 | Painchaud et al. |
| 2002/0092525 A1 | | 7/2002 | Rump et al. |
| 2002/0141901 A1 | | 10/2002 | Lewis et al. |
| 2002/0197390 A1 | | 12/2002 | Lewis et al. |
| 2003/0008407 A1 | | 1/2003 | Fu |
| 2003/0008788 A1 | | 1/2003 | Sonnenberg et al. |
| 2003/0078511 A1 | | 4/2003 | Hanson, III |
| 2004/0215402 A1 * | | 10/2004 | Hsiung et al. ................. 702/22 |

OTHER PUBLICATIONS

Doleman, et al., "Trends in odor intensity for human and electronic noses: Relative roles of odorant vapor pressure vs. molecularly specific odorant binding," Proc. Natl. Acad. Sci. USA, vol. 95, Issue 10, pp. 5442-5447, 1998.

(Continued)

*Primary Examiner*—Jill Warden
*Assistant Examiner*—Dwayne K Handy
(74) *Attorney, Agent, or Firm*—Kris T. Fredrick

(57) ABSTRACT

A substance detection system having an electronic nose and classifier. The system may extract feature from the electronic signals representing the smells from the electronic nose sensing an unknown substance. The features may be formatted as smellprints that are synthesized as data. The features may be classified, and in a binary tournament fashion, as an illustrative example, may be mapped to be compared or correlated with features of known substances. The known substance or substances having the highest scores for good mapping, comparison or correlation with the sensed substance, may be reviewed in view of decision criteria to determine an identification of the sensed substance.

3 Claims, 15 Drawing Sheets

OTHER PUBLICATIONS

Harris, et al., "Resistance characteristics of conducting polymer films used in gas sensors," Sensors & Actuators B, vol. 42, pp. 177-184, 1997.

Severin, et al., "An investigation of the concentration dependence and response to analyte mixtures of carbon black/insulating organic polymer composite vapor detectors," Anal. Chem., 72, pp. 658-688, 2000.

Wilson et al., "Chemical Sensors for Portable, Handheld Field Instruments," IEEE Sensors Journal, vol. 1, No. 4, pp. 256-274, Dec. 2001.

http://www.sensormag.com/articles/0800/56/main.shtml, "Sensors—Aug. 2000—The Cyranose Chemical Vapor Analyzer," Kavlico, 9 pages, printed Apr. 7, 2004.

* cited by examiner

|  | C | M | A | N |
|---|---|---|---|---|
| Final Activation | 9 | 0 | 31 | 0 |
| Initial Response | 20 | 3 | 15 | 2 |
| Combined Classifier | 28 | 2 | 10 | 0 |

Figure 11

|  | Jet Fuel | Max Flight | MobileJet | Octaflo | Skydrol |
|---|---|---|---|---|---|
|  | C M A N | C M A N | C M A N | C M A N | C M A N |
| FA | 8 0 0 0 | 0 0 8 0 | 0 0 8 0 | 0 0 8 0 | 1 0 7 0 |
| IR | 8 0 0 0 | 4 1 3 0 | 2 1 4 1 | 5 0 3 0 | 1 1 5 1 |
| FA+IR | 8 0 0 0 | 8 0 0 0 | 3 1 4 0 | 5 0 3 0 | 4 1 3 0 |

Figure 12

|  | C | M | A |
|---|---|---|---|
| Final Activation | 28 | 12 | 0 |
| Initial Response | 28 | 12 | 0 |
| Combined Classifier | 33 | 7 | 0 |

Figure 13

|  | Jet Fuel | Max Flight | MobileJet | Octaflo | Skydrol |
|---|---|---|---|---|---|
|  | C M A | C M A | C M A | C M A | C M A |
| FA | 8 0 0 | 7 1 0 | 3 5 0 | 8 0 0 | 2 6 0 |
| IR | 8 0 0 | 6 2 0 | 3 5 0 | 8 0 0 | 3 5 0 |
| FA+IR | 8 0 0 | 8 0 0 | 4 4 0 | 8 0 0 | 5 3 0 |

Figure 14

|  | C | M | A | N |
|---|---|---|---|---|
| Final Activation | 9 | 0 | 31 | 0 |
| Initial Response | 21 | 3 | 14 | 2 |
| Combined Classifier | 25 | 3 | 11 | 1 |

*Figure 15*

|  |  | Jet Fuel | Max Flight | MobileJet | Octaflo | Skydrol |
|---|---|---|---|---|---|---|
|  |  | C M A N | C M A N | C M A N | C M A N | C M A N |
| FA |  | 8 0 0 0 | 0 0 8 0 | 0 0 8 0 | 0 0 8 0 | 1 0 7 0 |
| IR |  | 8 0 0 0 | 6 1 1 0 | 2 1 4 1 | 4 0 4 0 | 1 1 5 1 |
| FA+IR |  | 8 0 0 0 | 8 0 0 0 | 2 1 4 1 | 4 0 4 0 | 3 2 3 0 |

*Figure 16*

|  | C | M | A |
|---|---|---|---|
| Final Activation | 28 | 11 | 1 |
| Initial Response | 28 | 8 | 4 |
| Combined Classifier | 35 | 5 | 0 |

*Figure 17*

|  |  | Jet Fuel | Max Flight | MobileJet | Octaflo | Skydrol |
|---|---|---|---|---|---|---|
|  |  | C M A | C M A | C M A | C M A | C M A |
| FA |  | 8 0 0 | 7 0 1 | 5 3 0 | 8 0 0 | 0 8 0 |
| IR |  | 8 0 0 | 6 1 1 | 5 2 1 | 8 0 0 | 1 5 2 |
| FA+IR |  | 8 0 0 | 8 0 0 | 7 1 0 | 8 0 0 | 4 4 0 |

*Figure 18*

SUBSTANCE DETECTION SYSTEM

BACKGROUND

The present invention pertains to sensing and particularly to the detection of substances. More particularly, the invention pertains to classification of detected substances.

There appears to be a need for a portable substance detection system, notably for detecting fluids, which may include an electronic nose or smell sensor having good selectivity and sensitivity.

SUMMARY

The invention provides an approach for robust detection of analytes using composite sensors while increasing selectivity and sensitivity. An illustrative example may involve several complementary parts. The one part may be to extract class-dependent information from the sensor's initial response at a sample draw. Another part may be to advance the discriminatory tools applied on raw data by developing high margin classifiers. The term "substance" in the present patent document may be understood and used in an inclusive and broad sense to mean a fluid, compound, analyte, particle, material, or other matter that may be present in chemical vapor phase.

BRIEF DESCRIPTION OF THE DRAWING

FIGS. 11-18 show tables of detection results relative to various classifications and decision criteria;

DESCRIPTION

Figure 1:
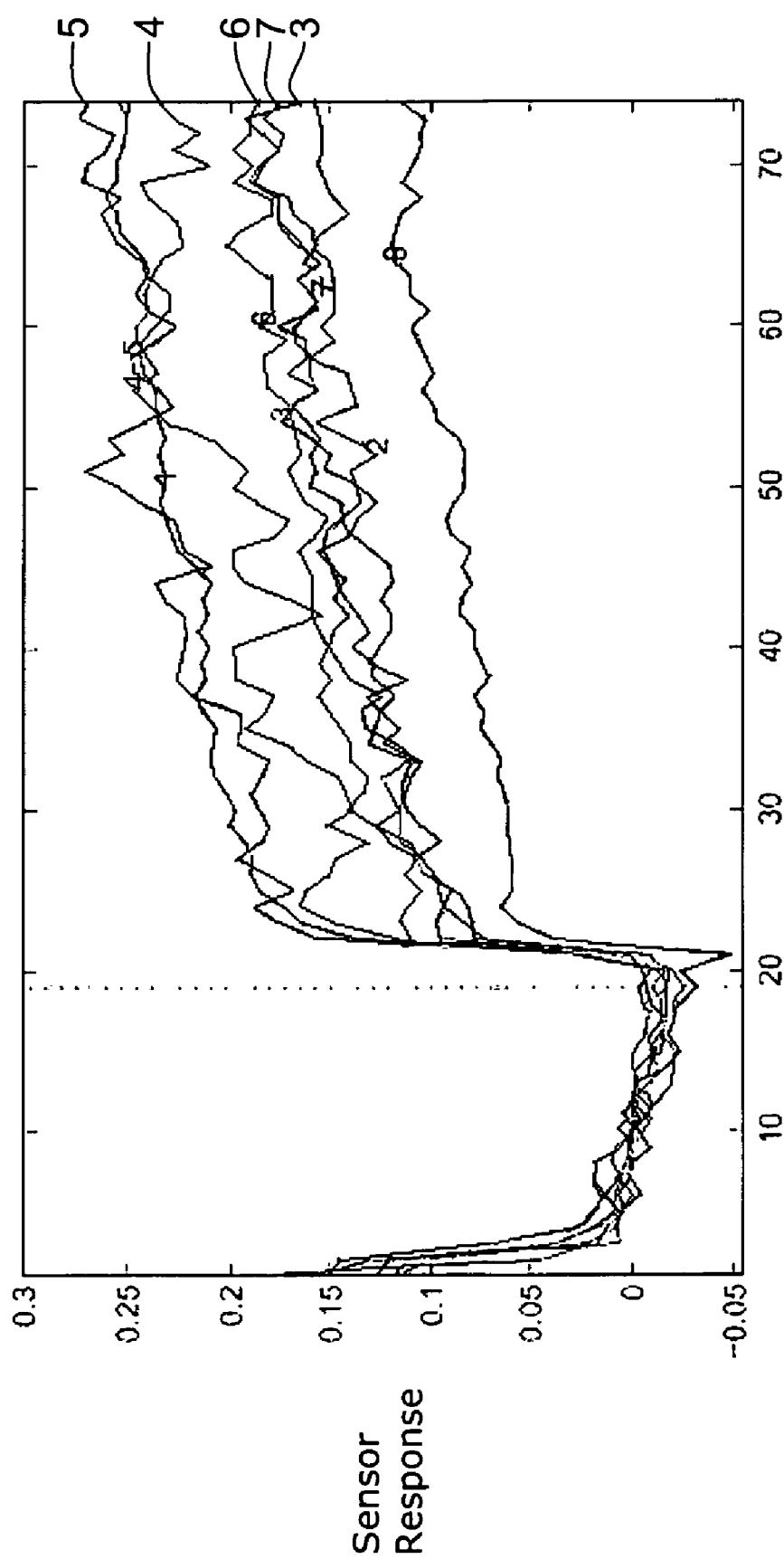
FIGS. 1-5 show baseline and sample draw signal diagrams from an electronic nose proximate to five different known substances.
Figure 2:
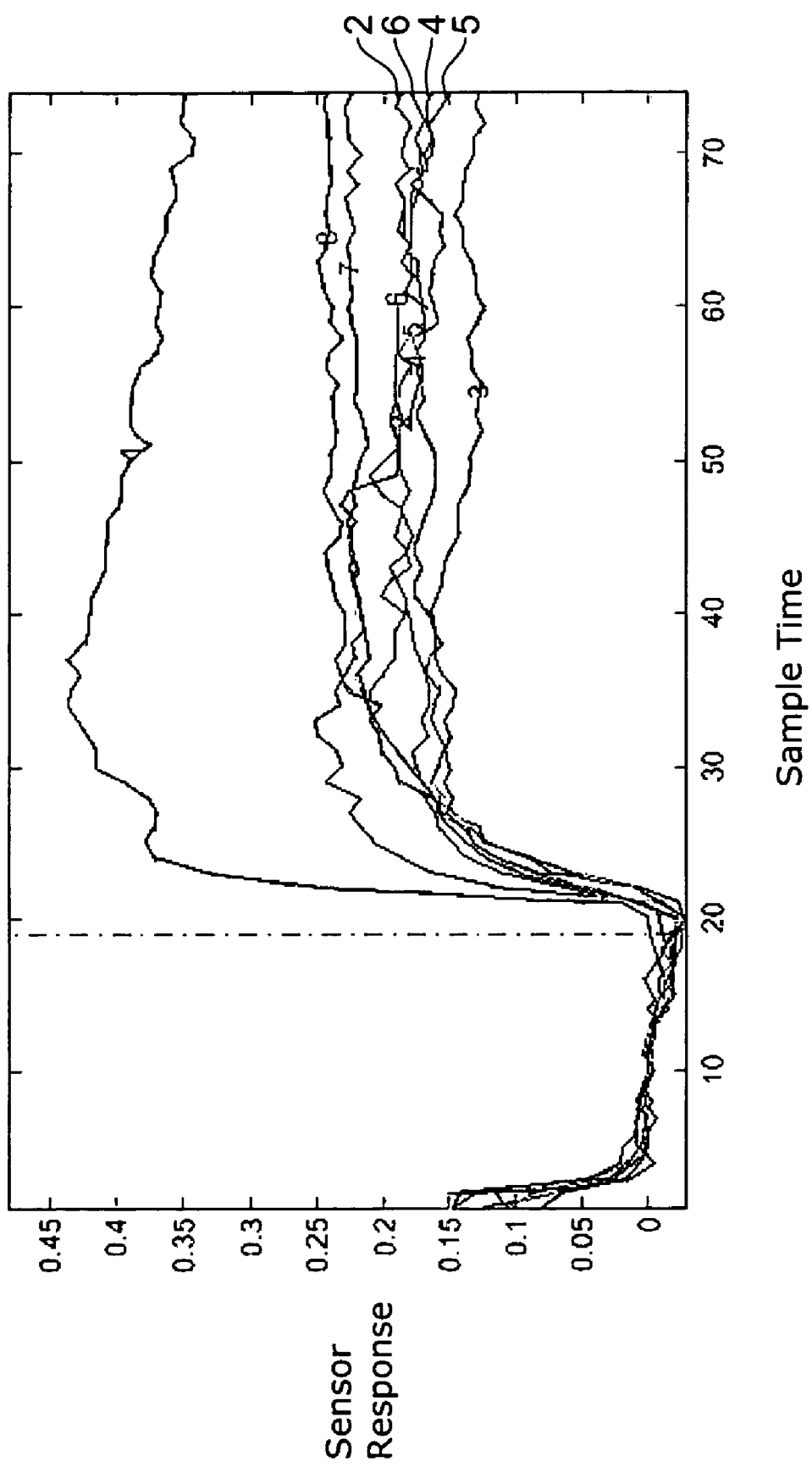
Figure 3:
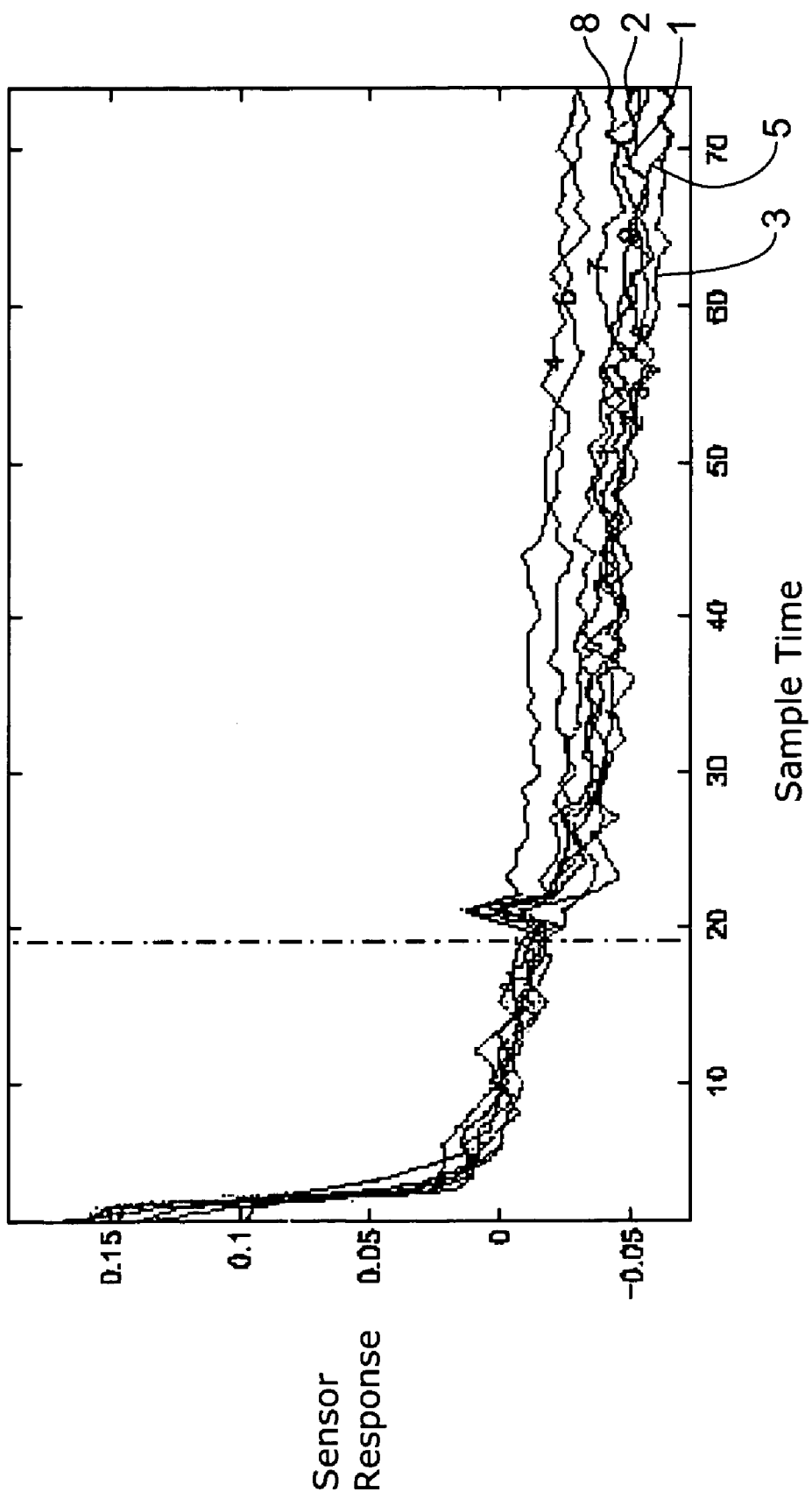
Figure 4:
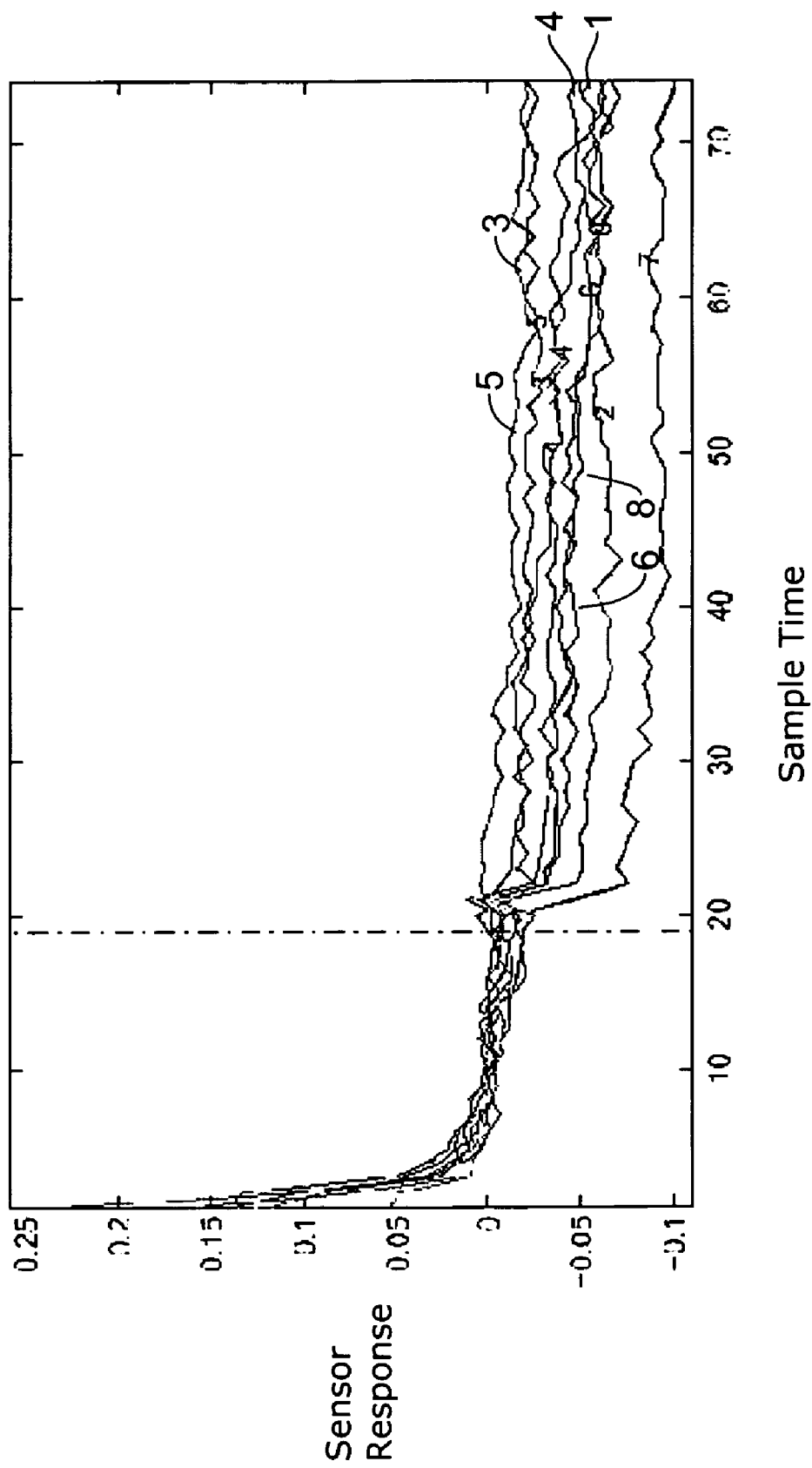
Figure 5:
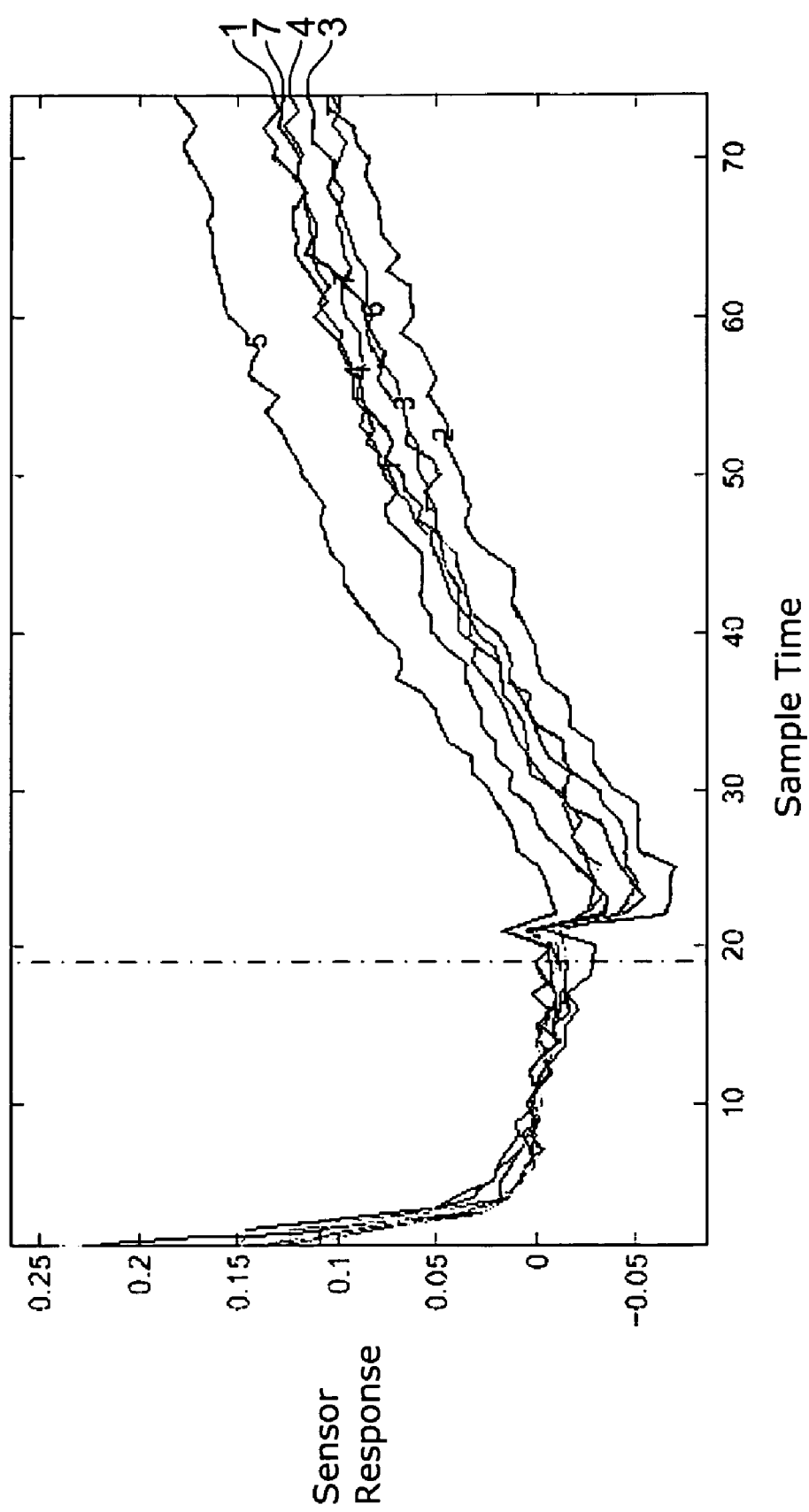
Figure 6:
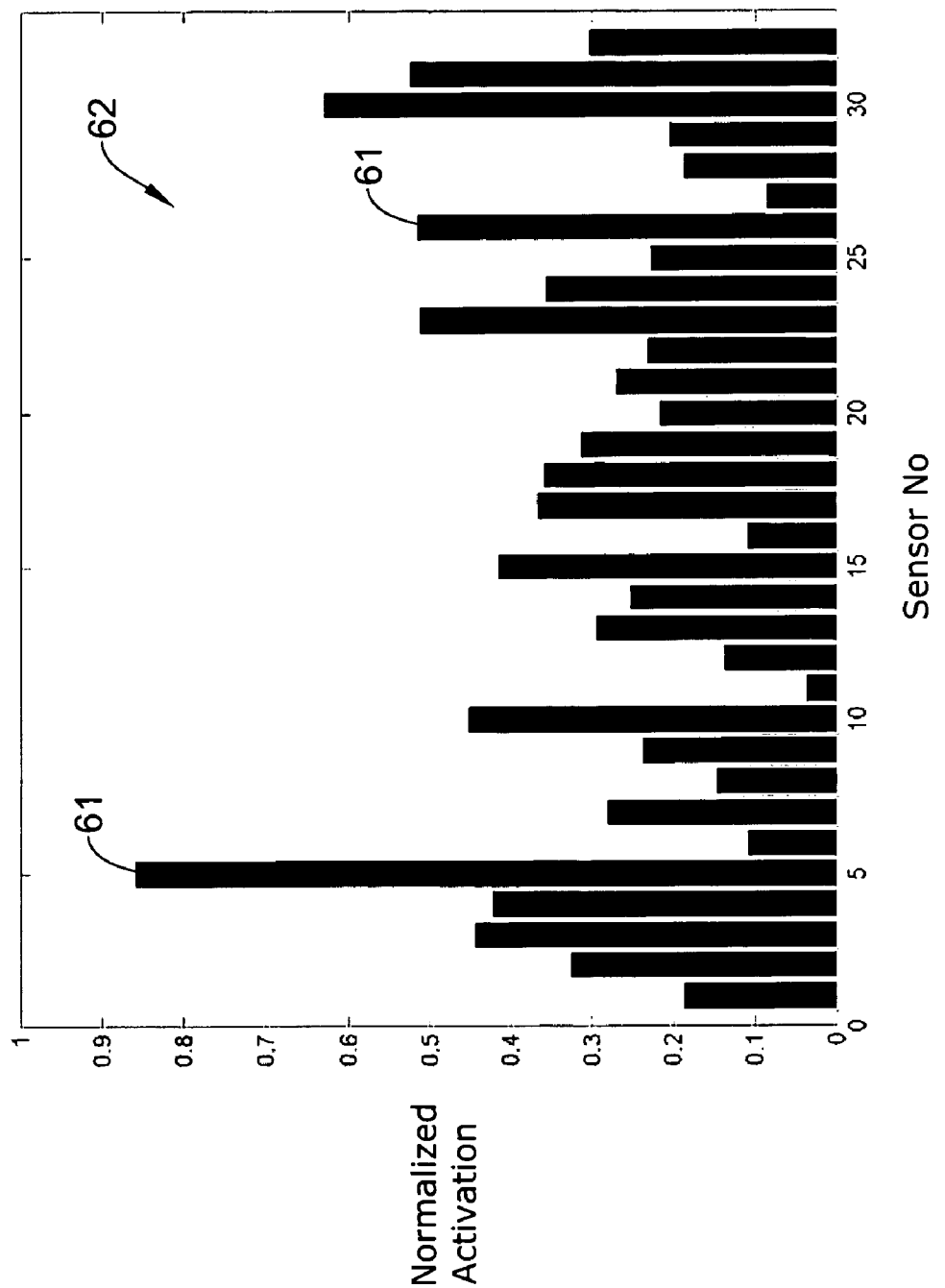
FIGS. 6-10 are smellprints of the five known substances.
Figure 7:
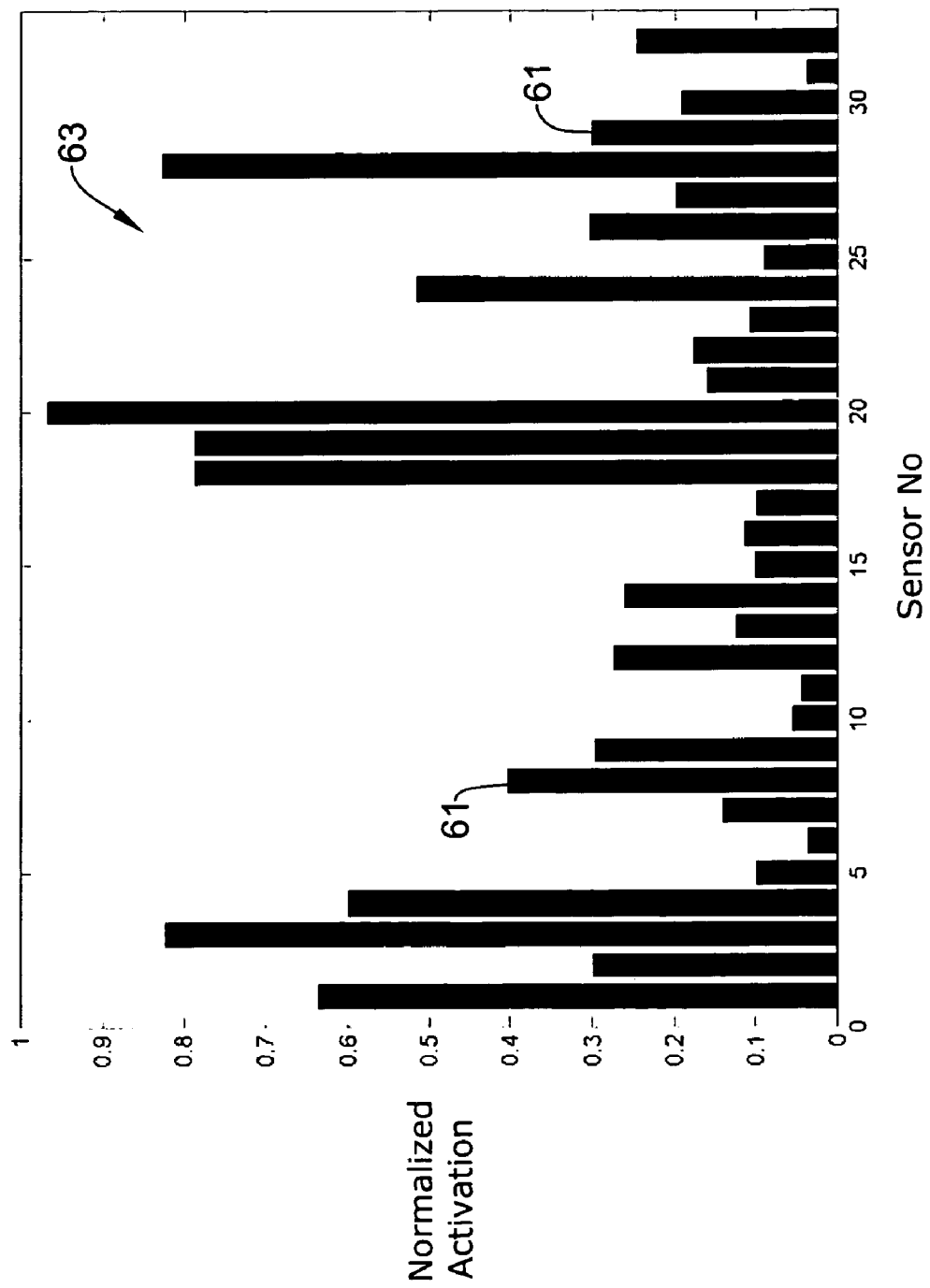
Figure 8:
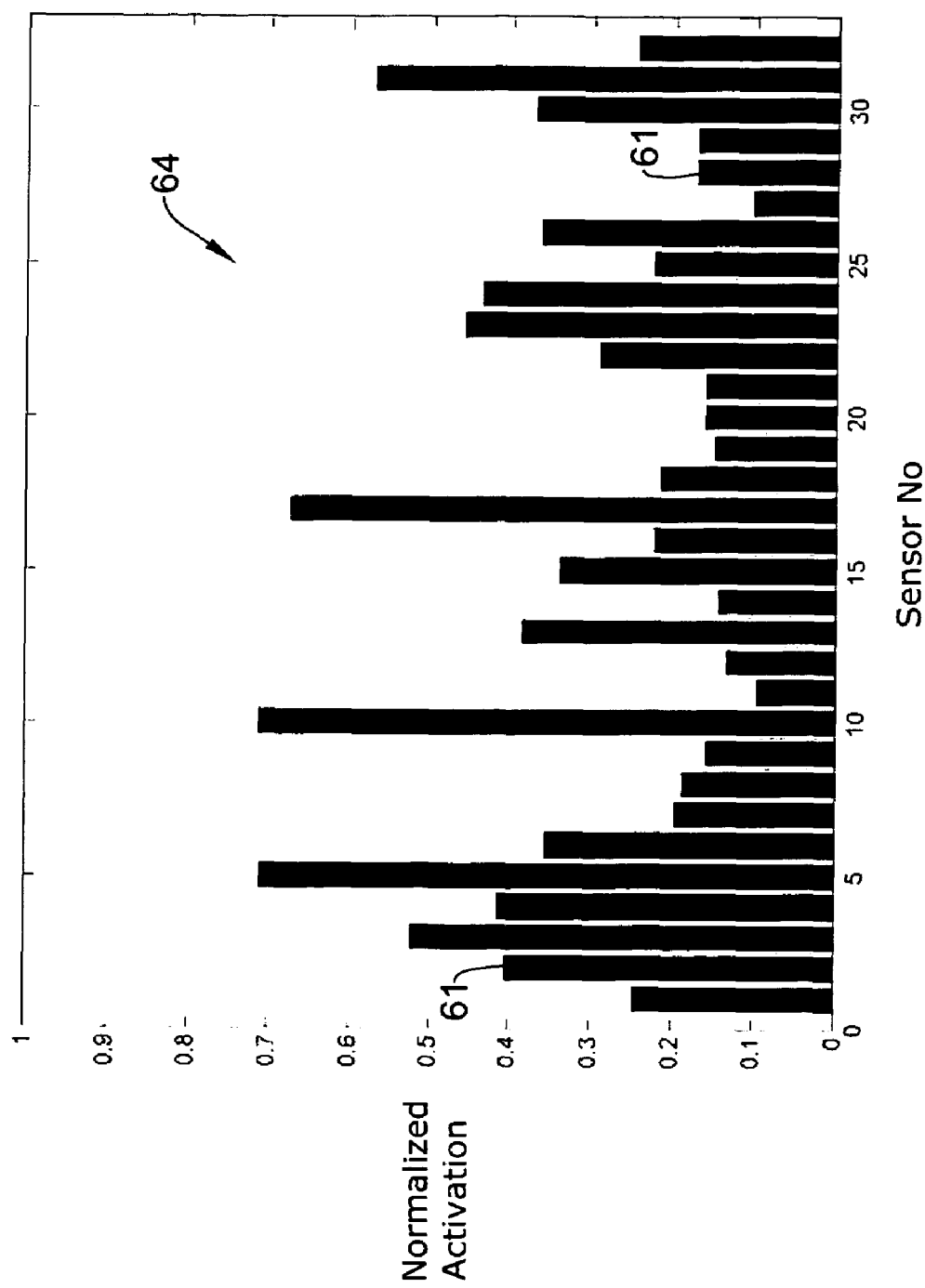
Figure 9:
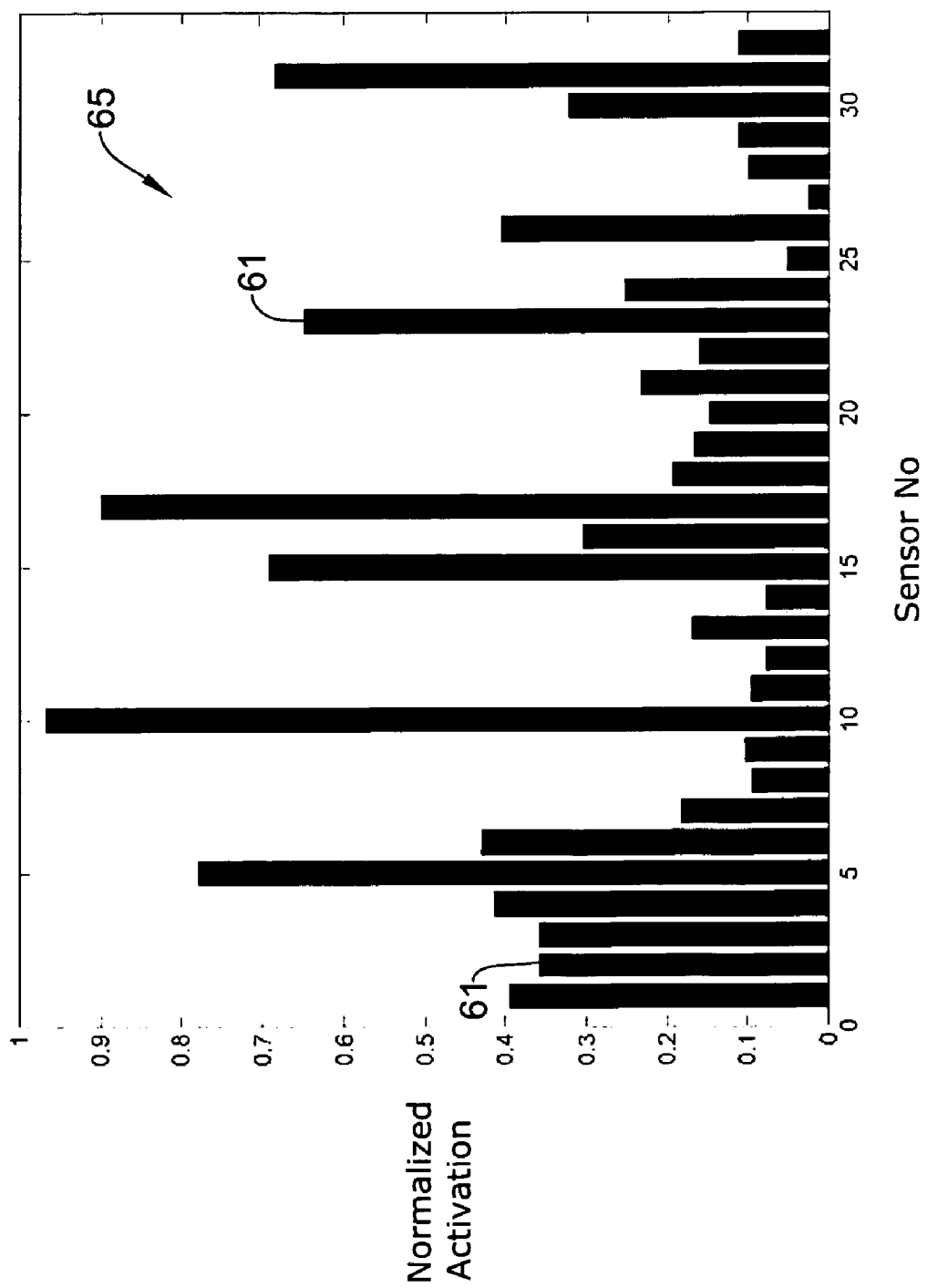
Figure 10:
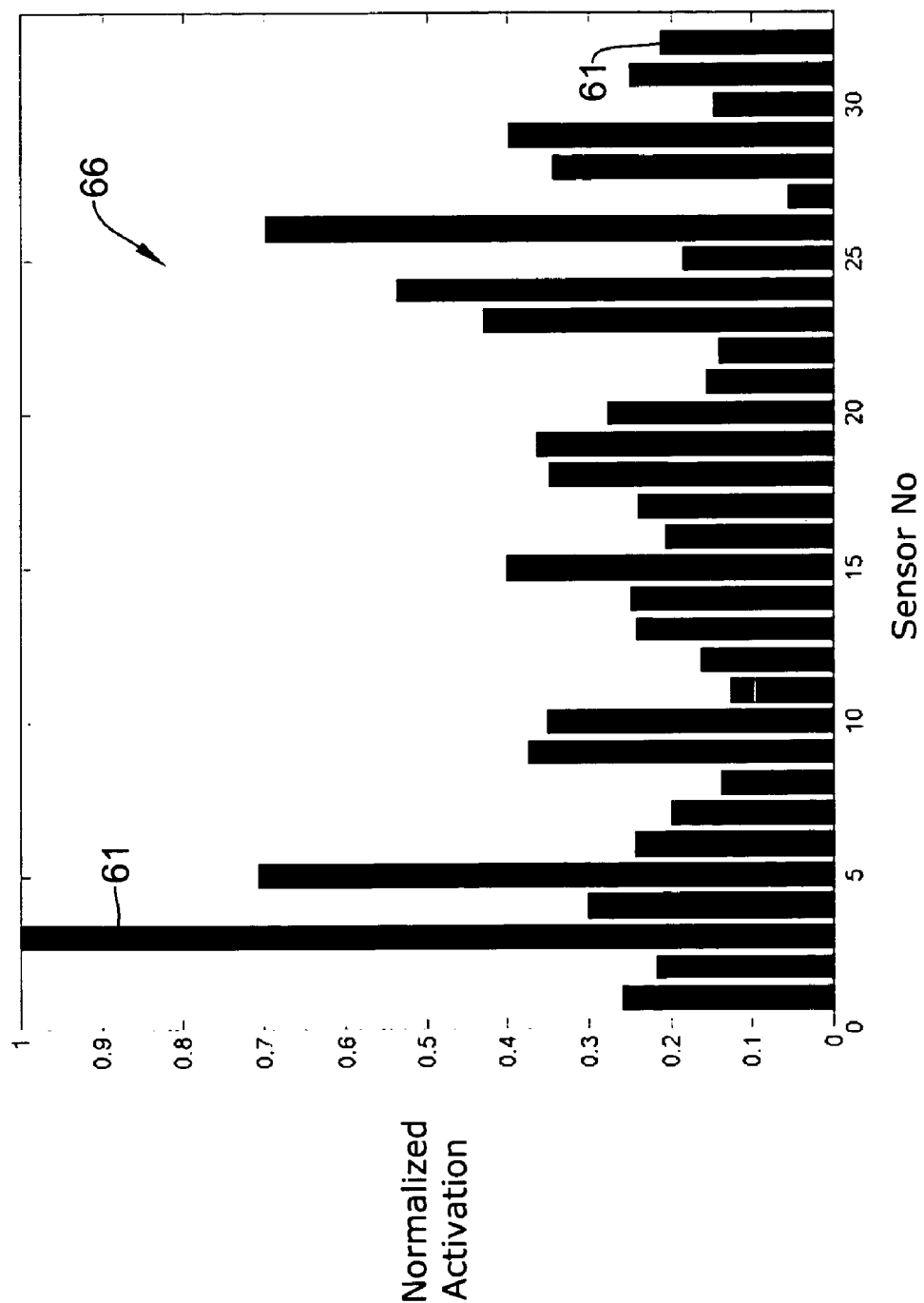

The invention, i.e., the substance detection and classification system, may include generating a smellprint which is based on initial reactions of the chemiresistors rather than the bulk relative resistance change. The invention may also present a robust classification approach employing a support vector machine (SVM) process. Various combinations of smellprints—including their projections to a small number of principal components—may be analyzed. Binary support vector machine classification results may be filtered through several different mechanisms: a set threshold on the total vote, and a winner-take-all method. The classification accuracy may be determined through the leave-one-out (LOO) procedure.

The system may provide a smellprint of a substance derived from polymer-based electronic nose, and a robust classification method. The system may be used for identifying five, more or less, compounds. The system could also be used to detect the presence of one compound. Results may be obtained in terms of improved detection at low concentrations and reduced false alarm rates.

For portable substance detection systems employed as electronic noses, selectivity and sensitivity remain as primary features attractive for their wide acceptance and use. Selectivity refers to the system's ability to detect the presence of an analyte of interest over the detection of what is not of interest. This property may be tuned in the design and manufacturing process of the sensor to a certain degree. However, the tuning then may limit the possible areas of application of the sensor.

The definition of sensitivity varies depending on the task. If the task is classification, sensitivity may refer to the detection threshold of a system in terms of chemical concentration. If however the task is regression, then sensitivity may refer to the system's ability to measure the smallest increment in chemical concentration, or partial pressure.

In recent years, there has been extensive research conducted in optimizing the physical properties of substance detection systems to achieve robustness by improving selectivity and sensitivity characteristics. The approaches vary from doping the sensors with various metals to increasing precision in grain or pellet sizes. In addition, the successes in miniaturization have led to the development of sensor arrays. Sensor arrays may permit increased selectivity by including more sensors that are tuned for different analytes. Redundancy in sensor arrays may also help in increasing the signal to noise ratio. However, in conducting polymers this advantage is masked by the increased noise in DC measurements of the resistance.

Another focus may be on data analysis and algorithm development that lead to improvements in selectivity and sensitivity. The approach may be demonstrated on a polymer-based electronic nose sensor for detecting five chemicals used in aerospace applications, such as gas turbine oil, hydraulic fluid, two types of deicing fluids, and jet fuel.

The system's approach for robust classification while increasing sensitivity may be two fold. The first is to extract class-dependent information from the sensors in addition to the one-dimensional "smellprint" which may be provided by an off-the-shelf product. The second is to advance the discriminatory tools applied on raw data with classification algorithms.

"Smell-detectors" or "electronic noses" are substance detecting devices based on a technique of full expansion which may use the absorption by polymeric membranes of analytes present in fluids or other substances. The absorption of the analytes by the polymeric membranes may generate an alteration of its physical properties, such as density, thickness, refractive index, resistivity, and the like.

Typically, an electronic nose or smell-detector may be composed of many sensors made from different polymer compositions, each having its own reaction to the presence of a given substance. Electronic noses or smell-detectors generally may measure the change in resistivity of the polymer membranes. However, since polymers are rarely conductive, it may be necessary to mix conductive particles, for example, carbon-black, to the polymeric material for increasing the conductivity of the membrane.

The electronic nose or smell-detector may consist of an array of polymer films embedded with conductive or resistive material. When exposed to substance such as a fluid, e.g., a gas, as applied to the present system, the polymer films may swell or contract thereby leading to a change in the DC electrical resistance of the film. The DC resistance across each of the films in the array may be sampled at approximately uniformly-spaced times resulting in a smellprint. The baseline sample draw as well as the purge periods may be marked.

An example of an off-the-shelf electronic nose may be a Cyranose® 320, available from Cyrano Sciences Inc., which is a device that may use polymer composite sensors that swell or contract when exposed to, for example, a vapor-phase analyte. It may include an array of 32 sensors, each of which consists of a pair of electrical contacts that are bridged by a composite film. Typically the film for each sensor may be made of a composite of a non-conducting polymer and conductive carbon black particles. When the film absorbs vapor analytes and swells, the conductive pathways in the film are broken and the resistance of the composite film changes. The change in resistance between the electrical contacts may be used as the output of the sensor. The film may be regarded as a chemiresistor. Since each sensor in the array contains a unique polymer, there may be a reproducible combination of resistances or a smellprint for each vapor mixture. Polymers with a range of properties can be chosen so that the sensor array may be used to distinguish many different types of substances. The responses from the chemiresistors may then be measured as a bulk relative resistance change ($R_{max}/R_{baseline}$), and be used to form a smellprint. An electronic nose having a number of sensors other than 32 may be used.

The 32-element or other number-element smellprint vector of the electronic nose may then be used for detecting, for instance, certain chemicals. There may be two factors relative to this approach. First, the final activation values may be dependent on the duration of sample draw, and second, the variance of final activation values over many exposures may be notable. These characteristics may cause chemical detection and repeatability issues. To alleviate these characteristics, additional features may be extracted from sensor signals as an alternative to, or in addition to, the original smellprint.

The initial rather than the final sensor response signal may be used as the smellprint. The signal preprocessing and feature extraction algorithms of the detection system that are developed may allow capturing the initial change of resistivity at the beginning of the sample draw period which provides unique and consistent signatures for different chemicals. In addition, the smellprint formed with initial sensor responses does not necessarily suffer from the problems mentioned for the final activation case. This additional smellprint may become very important especially at very low headspace concentrations where the bulk relative resistance change is either very low—sometimes due to short sample draw duration—or not consistent.

The chemical signatures formed based on the initial sensor responses may be unique and consistent. The results show that the classification performance achieved using only the initial response signatures may be comparable to or better than the one obtained with the original smellprint. When the two sets are combined, significant improvements in classification performance may be noted. For classification, the method of support vector machine may be employed. This kernel-based technique is shown to be more powerful and robust than the ones included with other electronic noses such as the Cyranose® 320 system.

The data set used to develop and test the algorithms may be obtained from various tests. Five compounds, as an illustrative set of compounds, may be considered: Mobil Jet II™—turbine oil, Skydrol LD—4™—hydraulic fluid, Octaflo™ and Maxflight™—deicing fluids, and Jet A™—jet fuel. Eight exposures for each compound may be analyzed. The typical signals received from polymer sensors during the baseline and sample draw periods are shown in FIGS. 1 through 5 for five different compounds. Each line in each figure corresponds to a different exposure of the same chemical. Notice that the signal amplitude is very low for some chemicals such as Mobil Jet™ and Skydrol™. Also note that the sensor response varies greatly from one exposure to another.

FIGS. 1 through 5 show the baseline and sample draw signals for the following compounds, Maxflight™, Jet A™, Mobil Jet™, Skydrol™ and Octaflo™, respectively. The exposures may be numbered 1-8 in each of the FIGS. 1-5. Any other number of compounds and other quantities of exposures may be utilized. FIGS. 6 through 10 show smellprints 62, 63, 64, 65 and 66 formed based on the initial changes in the resistivity of the electronic nose's array of polymer composite sensors for the cases of Maxflight™, Jet™, Mobil Jet™, Skydrol™ and Octaflo™, respectively. These figures illustrate smellprints based on the initial responses of sensors 1-32 (i.e., sensor no.) of the electronic nose for the respective substances. The combinations of magnitudes 61 of normalized activation shown in smellprints may be unique to the substance or compound detected by the electronic nose.

Support vector machines (SVM) are powerful tools for data classification. Classification may be achieved by a linear or nonlinear separating surface in the input space of the data set. A subset of data may be used to form the set of support vectors which define the separating surface.

Given an l-by-l kernel matrix K, a binary SVM classifier may be trained for the following formulation:

$$\text{minimize } \frac{1}{2}\sum_{i=1}^{l}\sum_{j=1}^{l}\alpha_i\alpha_j y_i y_j K(x_i, x_j) - \sum_{i=1}^{l}\alpha_i$$

$$\text{subject to: } 0 \leq \alpha_i \leq C, \sum_{i=1}^{l}\alpha_i y_i = 0$$

where l is the number of training examples, $y_i$ is the label (+1 for positive example, −1 for negative) for the i-th training example ($x_i$) and $K(x_i, x_j)$ denotes the value of the kernel function for the i-th and j-th examples of x.

The SVM may maximize the margin distance between the nearest positive and negative examples (in kernel feature space), which has been shown to lead to excellent generalization performance. The tests may be conducted using two different smellprints, which include the final activation data (FA smellprint), and the initial response data (IR smellprint). Also included may be the results for the combined case (FA+IR). The effect of using smellprints directly in classification versus using a small number of principal components may be useful. Support vector machine classification results may be filtered through a set threshold and a winner-take-all mechanism.

Because one may employ a binary classifier on a multiple class problem, a set of classifiers is trained and the pair-wise voting scheme may be used for final labeling of each case. In pair-wise voting, k(k−1)/2 classifiers may be needed for each pair-wise contest. In the present illustrative example, ten classifiers may be built for five compounds, k=5.

The classification accuracy may be determined through the leave-one-out (LOO) procedure. That is, the data from one exposure for each compound may be withheld and the SVM be trained with the remaining exposures. The resulting classifier may then be tested with the data that it has not seen during the training.

Sensor values may be obtained with a detection threshold. In this case, the FA and IR smellprints may be used directly in training. The detection threshold may be set to 0.75. This means that for a positive detection to be made, the pair-wise voting result may be larger than or equal to 75 percent. The FA smellprint may result in a very high ambiguous detection rate while the IR data may provide much higher correct classification rate. The combined classifier may give better results than either one alone, the robustness may be improved.

The table of FIG. 11 shows the overall classification results. The columns "C", "M", "A", and "N" indicate "Correct Classification", "Misclassification", "Ambiguous Classification", and "No Detection", respectively. The meanings of "Correct Classification" and "Misclassification" are literal. "Ambiguous Classification" means that one other compound besides the correct one is voted high. "No Detection" means no compound received votes higher than the threshold. The results are given over 40 exposures, i.e., 8 exposures each for 5 compounds. The table of FIG. 11 reveals detection results with the detection threshold (theta) equal to or greater than 0.75. The table of FIG. 12 details the results per compound. One may note that although the overall performance is poor, Jet A™ fuel is identified correctly 100 percent in all three cases. The combined classifier appears to improve the results dramatically for the case of Maxflight™ as well. However the remaining three compounds are not detected about half the time. This table shows detection results for each compound with theta=0.75.

Using sensor values with a winner-take-all approach, the FA and IR smellprints may be used directly for classification again, but this time the winner-take-all procedure may be applied to the voting results. Hence the "N" column (No Detection) may be removed from the relevant tables.

The results presented in the tables of FIGS. 13 and 14 show that both the overall accuracy and the individual compound detection rate improve significantly in this case. However, while the ambiguous classification is reduced, some of those cases may be included in the misclassified cases column. The table of FIG. 13 shows detection results with the winner-take-all approach. The table of FIG. 14 shows detection results for each compound with the winner-take-all approach.

The principal components with a detection threshold may be noted. It appears that if the same classification training performance could be achieved using a smaller number of features, a better generalization would be achieved. To this end, the 32 dimensional smellprint data may be processed for its principal components. SVM may be retrained using only the first ten retained principal components. The tables of FIGS. 15 and 16 show the results for the case of using a threshold of 0.75 on the pair-wise voting results. FIG. 15 shows detection results with principal components and theta=0.75. FIG. 16 shows detection results for each compound with principal components and theta=0.75.

The principal components with the winner-take-all approach may be noted. This case shows the results of using 10 principal components and the winner-take-all procedure. The best overall results may be achieved in this case. 35 out of 40 cases are correctly identified. The table of FIG. 17 shows detection results with principal components and the winner-take-all approach. The table of FIG. 18 shows the detection results for each compound with principal components and winner-take-all.

Electronic nose sensitivity and selectivity may be noted. Improvements on these areas include data preprocessing, feature extraction, and a classification algorithm. Headspace data from five compounds used in aerospace applications may be analyzed. A new smellprint based on the initial reactions of the chemiresistors in addition to the bulk relative resistance change may be computed as a way to increased robustness. Also presented may be a classification approach employing the support vector machine process. Various combinations of the two smellprints-including their projections to a small number of principal components may be analyzed. The binary support vector machine classification results may be filtered through two different mechanisms, which may include a set threshold on the total vote, and a winner-take-all method.

When a small number of exposures are available (8 for each of the 5 compounds), the classification accuracy may be determined through the leave-one-out (LOO) procedure. The best results may be obtained when the binary support vector machine process is applied on a small set of features obtained through principal component analysis and the outcome may be determined through the winner-take-all approach. The new smellprint may provide better discriminatory information in most cases than the original smellprint.

An approach may incorporate the deciding between two possible candidates in comparison with a substance such as a fluid to be identified. The comparison may be with another substance that is similar for votes. A comparison of different substances may result in few votes or a small score. One sample or test datum may have features extracted to a SVM which is told of five possible substances. All 5 substances are looked at and compared as pairs with the sample, i.e., a binary comparison. The substance may be matched to one of the two such as a test case to substance 1 or substance 2. The test substance may be compared to the following pairs and one of the two may be picked in each comparison and the picked substance that gets most of the votes is the identifying substance. The pairs may include 1 and 2, 1 and 3, 1 and 4, 1 and 5, 2 and 3, 2 and 4, 2 and 5, 3 and 4, 3 and 5, and 4 and 5. Each number appears 4 times. The most selected number may have 4 votes which is the maximum. The vote may be 3 or there may be a tie of 3 of each. The base number of the total of different substances being paired off for comparison and selection may be other than 5.

From the electronic nose may be signals relative to a substance being sensed. The change in the electrical resistance across the polymer sensor as it is exposed to an analyte may constitute the raw data signal. Two types of smellprints may be extracted from the raw sensor data. An FA smellprint 14 (shown in FIG. 19) may refer to the smellprint formed based on the final activations of sensor array at the end of the sample draw. FA smellprint 14 may be computed as the change in the resistivity relative to the baseline resistivity, $\Delta R/R_{baseline}$. An IR smellprint 15 may be formed based on the initial response of the sensor array to the presence of an analyte. The IR smellprint 15 may take advantage of the transient response characteristics of polymer sensors. The sensor response within 6-10 samples following the introduction of analyte may be observed to be distinct to each analyte-sensor pair and consistent across many exposures. However, using this data for detection may require a robust feature extraction process of a module 13 (in FIG. 19) since the signatures formed during the transient can be subtle and the signal-to-noise ratio might be high.

Figure 19:
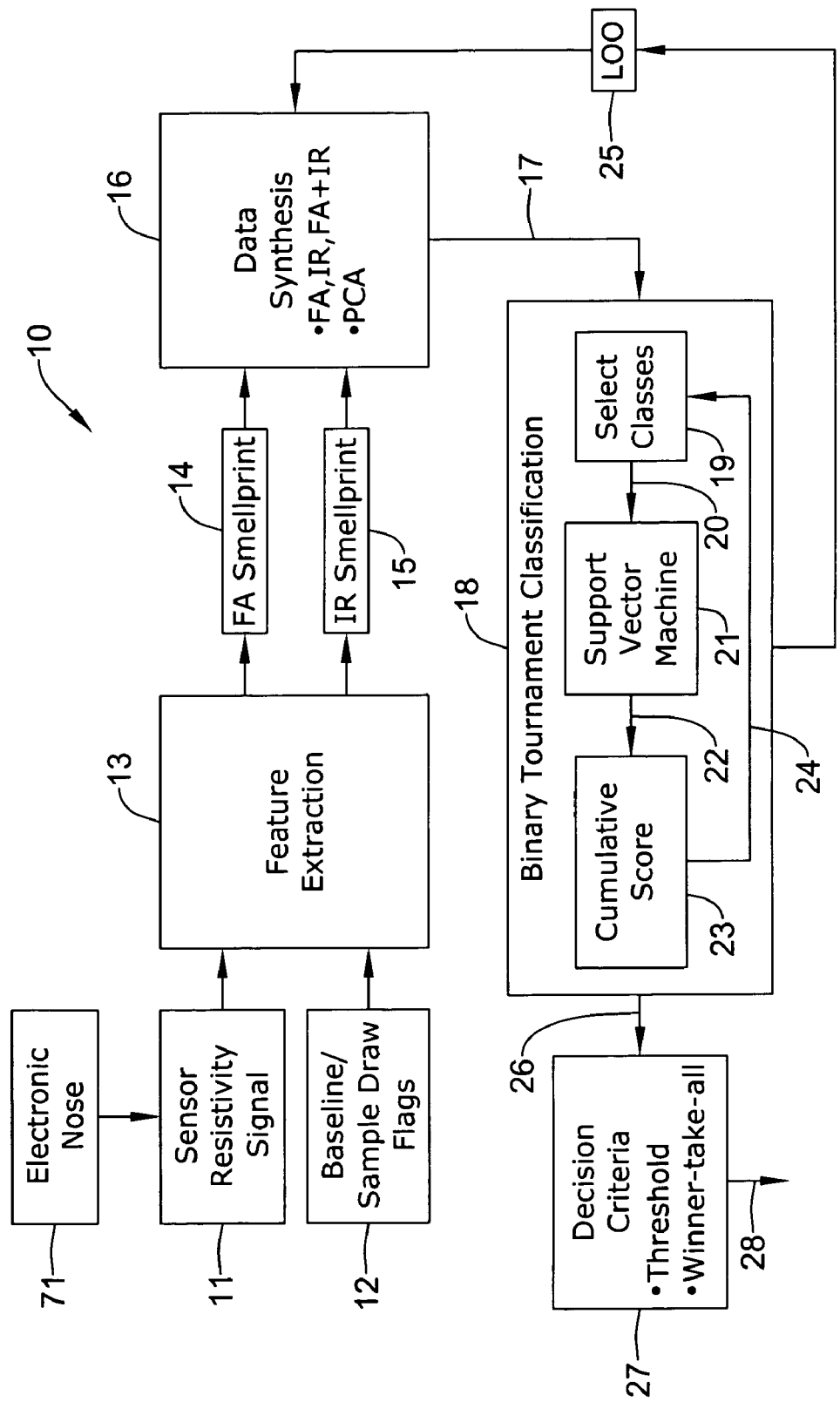
FIG. 19 shows an illustrative example of a substance detection system.

FIG. 19 shows an analyte (e.g., a target substance in a fluid) sensing and classification system 10. System 10 may be utilized to identify a sensed substance. A sensor resistivity signal 11 (31 in FIG. 20) and baseline/sample draw flags (33, 38 in FIG. 20) signal 12 may go to the feature extraction module 13 that may implement feature extraction. From module 13, FA smellprint 14 and IR smellprint 15 may go a data synthesis module 16. The data synthesis may incorporate and process FA, IR and FA+IR data plus the PCA (principal component analysis) for an output 17 to a binary tournament classification module 18. The synthesized data 17 may go to a select classes sub-module 19. Data 20 processed by sub-module 19 may go to a support vector machine 21. An output 22 from SVM 21 may go to a cumulative score sub-module 23 to be tabulated. An output 24 from sub-module 23 may go to the select classes module 19, thereby forming a feedback loop. There may be several outputs from module 18. One output 25 may be a leave-one-output (LOO) that goes to the data synthesis module 16. Another output 26 from module 18 may include binary data classification information that goes to a decision criteria module 27. The information or data output 26 may be processed by module 27 according to a threshold and/or winner-take-all criterion. An output 28 from module 27 may identify the substance sensed by the electronic nose.

Figure 20:
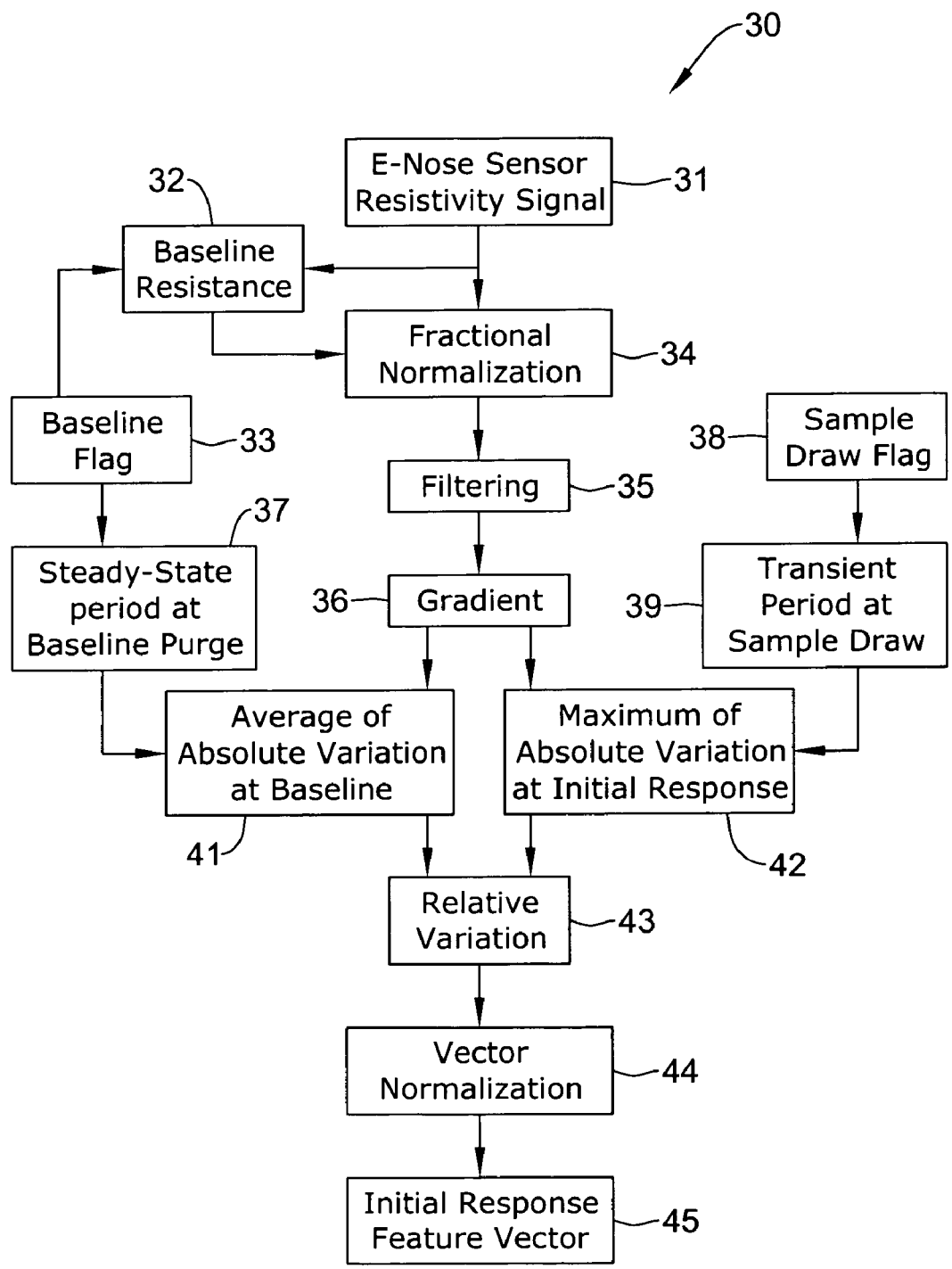
FIG. 20 is a diagram of a feature extraction mechanism.

FIG. 20 shows a module 30 with the steps, states, sub-modules or stages involved in the computation of IR smellprint 15 feature vector. Module 30 may have numerous aspects of the feature extraction module 13 of system 10 in FIG. 19. The raw sensor data may be an electronic nose sensor resistivity signal 31 (11 in FIG. 19) that may be taken in the form of time series data. The periods for baseline purge and sample draw may also be available. Sub-module 38 may be a sample draw flag. As a first step in the preprocessing the raw data 31, a baseline resistivity 32 may be computed. Sub-module 32 may be a processor. The corresponding portion of the time series data as marked by the baseline flag 33 may be used. The conventional approach of arithmetic averaging the baseline data for computing the baseline resistance 32 may be prone to failure, mainly because the baseline purge period 37 might contain high resistance data especially when successive measurements are taken with short purge periods in between. For this reason, a more robust method may be sought. Sub-module 37 may be a steady state period indicator at the baseline purge. In view of this, using the median which is more robust to outliers may be useful.

The fractional normalization 34 may be done by subtracting and dividing the raw sensor data from state 31 with the baseline resistance 32. Sub-module 34 may be a normalizer. This may generate a dimensionless and normalized sensor data, and remove the effect of the additive drift as well as the multiplicative drift that the sensor may experience.

The filtering 35 may be done next to remove noise across each exposure. Sub-module 35 may be a filter. The type of filter to be used at this stage may depend on the length of the baseline period and the length of the initial response region of interest. A filter whose edge effects do not extend to the transient region and the baseline region immediately preceding it may be useful. The output of filtering 35 may go through a gradient state 36. Sub-module 36 may be a gradient indicator.

The polymer sensors, when exposed to an analyte, swell or shrink thereby causing a change in the resistance. The magnitude of this change in a given time may vary depending on the sensor-analyte pair. Therefore, a rate of change may be computed next for each sample.

The baseline purge may bring the sensor volume to its nominal size. This state 37 may include an initial transient followed by a steady-state region. Once the sample draw is initiated at state 38, the sensor response may go through a transient period 39 followed by a steady-state 37 again—this time in the opposite direction. Sub-module 39 may be a transient period indicator at sample draw. For the IR smellprint 15, the average variation 41 at the steady-state 37 of the baseline purge with the gradient 36 output and the maximum variation 42 at the transient period 39 of the sample draw with the gradient 36 output may be used to compute a relative variation 43. This may be akin to computing a z-score for the sensor. The absolute maximum 42 of the relative variation 43 in the transient region 39 of sample draw may then be taken as the feature value representing the initial response of the sensor. Sub-module 43 may be a relative variation processor. A typical steady-state length 37 used for the baseline purge may be 10 samples and a typical length for the initial transient 39 may be 6 samples. Sub-module 41 may be an indicator of average of absolute variation at baseline. Sub-module 42 may be an indicator of maximum absolute variation at initial response.

Finally, the feature vectors may be normalized to account for variations across different exposures by dividing each vector by its norm. This step or sub-module may be called a vector normalization or normalizer 44. The IR smellprint 15 may then be formed as a 32 element vector at stage or indicator sub-module 45—one element for each sensor in the gas sensor array. However, more or less elements may be incorporated in the detection system 10.

Figure 21:
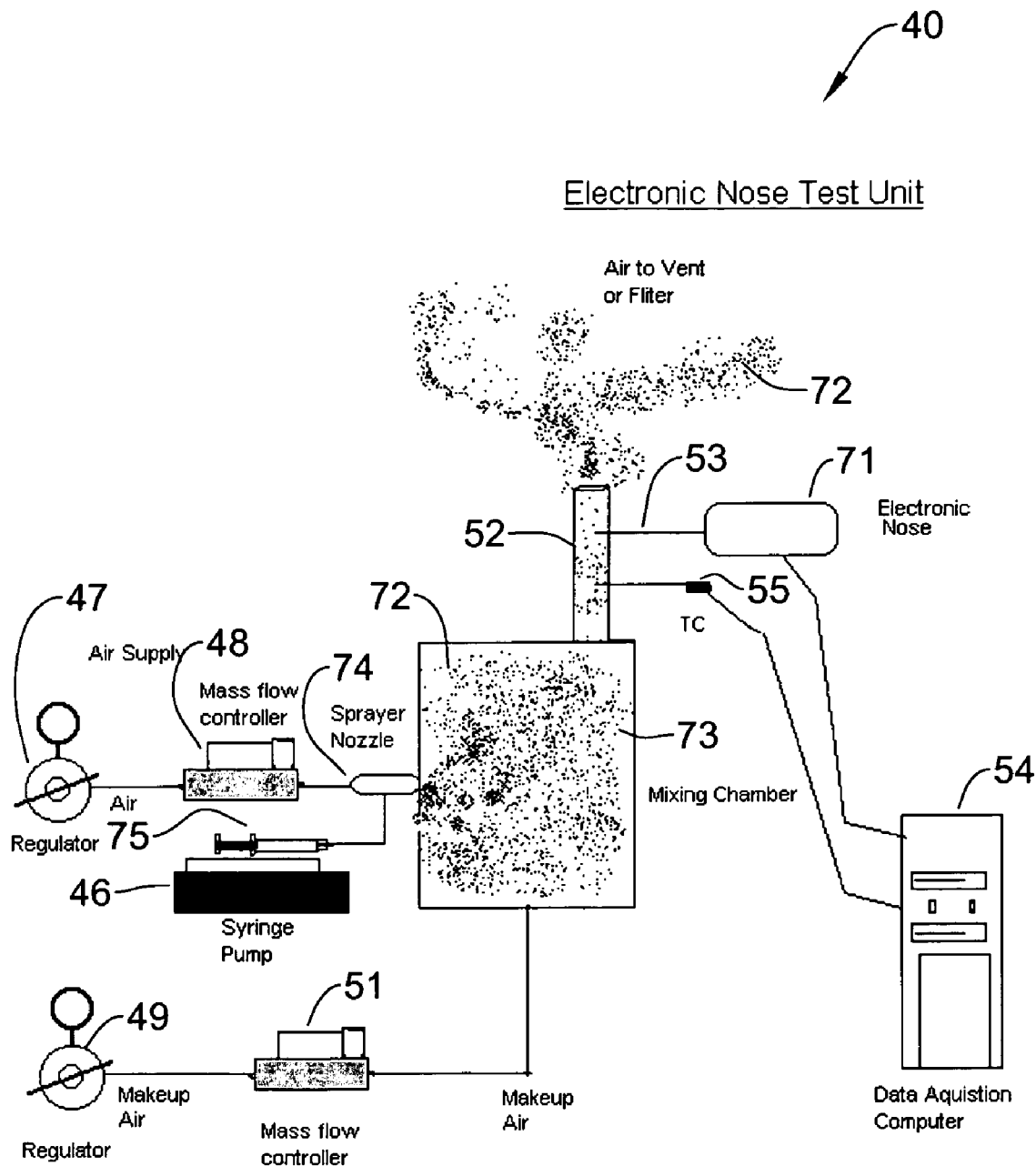
FIG. 21 shows a test set-up for a substance detection and identification system.

FIG. 21 shows a test system set-up 40 for evaluating an electronic nose 71 system. A mixture of air and fluid 72 may be inserted into a mixing chamber 73 by a sprayer nozzle 74. The fluid 72 fed by syringe pump 75 from supply tank 46 may go to sprayer nozzle 74. Also, air may be fed to nozzle 74 from a regulated air supply 47 via mass air flow controller 48. Additional air (i.e., make-up air) may be added to the mixing chamber 73 from a regulated air supply 49 via a mass air flow controller 51. On top of the mixing chamber 73 may be a "smoke-stack" like exhaust port 52. An inlet probe 53 of electronic nose 71 may be inserted into port 52 for detection of fluid 72. Electronic nose 71 may be connected to a data acquisition computer 54. Computer 54 may process the signals from nose 71 into signals that identify the fluid 72 particles. Computer 54 may have a substance detection system like one described in the present description. Also, a temperature sensor 55 may be situated in exhaust port 52 of chamber 73. A temperature signal from sensor 55 may be sent to computer 54 to provide temperature compensation for the substance detection system.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A substance detection system comprising:

an electronic nose;

a feature extraction module connected to the electronic nose;

a data synthesis module connected to the feature extraction module;

a classification module connected to the data synthesis module; and a decision criteria module connected to the classification module;

wherein the classification module comprises a support vector machine the feature extraction module provides a smellprint to the data synthesis module;

the smellprint comprises a final activation and initial response data;

the output classification module has an output for classification results;

the decision criteria module is for filtering the classification results; and wherein feature extraction module comprises:

a baseline flag;

a baseline resistance processor having a first input from the electronic nose and a second input from the baseline flag;

a fractional normalizer having a first input from the electronic nose and a second input from the baseline resistance;
a filter having an input connected to the fractional normalizer;
a gradient indicator having an input connected to the filter;
a steady-state period indicator at the baseline purge having an input connected to the baseline flag;
a sample draw flag;
a transient period indicator at sample draw having an input connected to the sample draw flag;
an indicator of average or absolute variation at baseline having a first input connected to the steady-state period indicator at baseline purge and a second input connected to the gradient indicator;
an indicator of maximum absolute variation at initial response having a first input connected to the transient period indicator at sample draw and having a second input connected to the gradient indicator;
a relative variation processor having a first input connected to the indicator of average of absolute variation at baseline and a second input connected to the indicator of maximum absolute variation at initial response;
a vector normalizer having an input connected to the relative variation processor; and
an initial response feature vector indicator having an input connected to the vector normalizer and an output connected to the data synthesis module.

2. Means for detecting a substance comprising:
means for sensing a substance via a smell;
means for converting the smell into at least one signal;
means for extracting features from the at least one signal;
means for mapping features to features of each of a plurality of known substances;
means for indicating a score of mapping for each of the known substances;
means for selecting the known substance having the highest score; and
means for determining whether the sensed substance is identified as the same as the known substance having the highest score;
wherein the means for determining comprises a criterion selected from a group of the threshold levels and winner-take-all criteria; and
the mapping of features is a binary tournament classification.

3. The means of claim 2, wherein the binary tournament classification comprises a support vector machine.

* * * * *